(12) United States Patent
Sunagawa et al.

(10) Patent No.: US 11,338,143 B2
(45) Date of Patent: May 24, 2022

(54) CONTROL APPARATUS FOR TREATING MYOCARDIAL INFARCTION AND CONTROL METHOD FOR TREATING MYOCARDIAL INFARCTION

(71) Applicant: Neuroceuticals, Inc., Tokyo (JP)

(72) Inventors: Kenji Sunagawa, Tokyo (JP); Shinya Miike, Tokyo (JP); Keita Saku, Tokyo (JP)

(73) Assignee: Neuroceuticals, Inc., Tokyo (JP)

( * ) Notice: Subject to any disclaimer, the term of this patent is extended or adjusted under 35 U.S.C. 154(b) by 7 days.

(21) Appl. No.: 16/359,515

(22) Filed: Mar. 20, 2019

(65) Prior Publication Data

US 2020/0298006 A1    Sep. 24, 2020

(51) Int. Cl.
*A61N 1/36* (2006.01)
*A61N 1/05* (2006.01)
*A61N 1/365* (2006.01)

(52) U.S. Cl.
CPC .......... *A61N 1/36114* (2013.01); *A61N 1/056* (2013.01); *A61N 1/36128* (2013.01); *A61N 1/36564* (2013.01)

(58) Field of Classification Search
CPC ............... A61N 1/36114; A61N 1/056; A61N 1/36128; A61N 1/36564
USPC .......................................................... 607/44
See application file for complete search history.

(56) References Cited

U.S. PATENT DOCUMENTS

| | | | |
|---|---|---|---|
| 2005/0143779 A1* | 6/2005 | Libbus | A61N 1/36139 607/9 |
| 2005/0288718 A1* | 12/2005 | Sunagawa | A61N 1/36114 607/9 |
| 2006/0052831 A1* | 3/2006 | Fukui | A61N 1/36114 607/9 |
| 2006/0293714 A1 | 12/2006 | Salo et al. | |
| 2007/0038259 A1* | 2/2007 | Kieval | A61N 1/36114 607/44 |

(Continued)

FOREIGN PATENT DOCUMENTS

JP    2008-546507 A    12/2008
JP    2019051021 A    4/2019

*Primary Examiner* — Carl H Layno
*Assistant Examiner* — Michael J Lau
(74) *Attorney, Agent, or Firm* — Finnegan, Henderson, Farabow, Garrett & Dunner LLP (57) ABSTRACT

A stimulation control unit that outputs a stimulation signal for reducing a myocardial workload to an electrode for stimulation inserted in a blood vessel running in the vicinity of the vagus nerve of a patient in order to stimulate the vagus nerve; a detecting unit that detects first biological information and second biological information of the patient; a setting unit that sets threshold information for determining a normal range of the first biological information and second biological information; and a determining unit that determines whether or not values of the detected first biological information and second biological information are within the normal range determined in the threshold information; where the stimulation control unit adjusts the intensity of the stimulation signal such that the values of the first biological information and second biological information are within the normal range, and the value of the second biological information is reduced by a predetermined ratio or more as compared to a value before the stimulation.

6 Claims, 5 Drawing Sheets

(56) References Cited

U.S. PATENT DOCUMENTS

| | | | |
|---|---|---|---|
| 2008/0015659 A1 | 1/2008 | Zhang et al. | |
| 2008/0046016 A1* | 2/2008 | Ben-David | A61N 1/36114 607/6 |
| 2008/0300642 A1* | 12/2008 | Inagaki | A61N 1/36114 607/14 |
| 2009/0018608 A1* | 1/2009 | Schwartz | A61N 1/36564 607/44 |
| 2010/0010556 A1* | 1/2010 | Zhao | A61N 1/36114 607/17 |
| 2010/0036447 A1* | 2/2010 | Zhang | A61N 1/36114 607/4 |
| 2010/0204741 A1* | 8/2010 | Tweden | A61N 1/3787 607/3 |
| 2010/0268333 A1* | 10/2010 | Gohean | A61M 60/258 623/3.14 |
| 2010/0274308 A1* | 10/2010 | Scott | A61N 1/36135 607/9 |
| 2011/0046432 A1* | 2/2011 | Simon | A61N 2/02 600/14 |
| 2011/0137370 A1 | 6/2011 | Gross et al. | |
| 2012/0035679 A1* | 2/2012 | Dagan | A61N 1/0553 607/14 |
| 2013/0072997 A1* | 3/2013 | Sanders | A61N 1/36114 607/18 |
| 2013/0237948 A1* | 9/2013 | Donders | A61N 1/36114 604/500 |
| 2014/0046407 A1* | 2/2014 | Ben-Ezra | A61N 1/36114 607/62 |
| 2014/0142590 A1 | 5/2014 | Masson | |
| 2015/0025298 A1* | 1/2015 | Sunagawa | A61N 2/02 600/14 |
| 2015/0039058 A1* | 2/2015 | Masson | A61N 1/0551 607/62 |
| 2016/0271394 A1* | 9/2016 | Sunagawa | A61N 1/36053 |

* cited by examiner

CONTROL APPARATUS FOR TREATING MYOCARDIAL INFARCTION AND CONTROL METHOD FOR TREATING MYOCARDIAL INFARCTION

TECHNICAL FIELD

Several aspects of the present invention relate to a control apparatus for treating myocardial infarction and a control method for treating myocardial infarction.

BACKGROUND TECHNOLOGY

Reperfusion therapy that reopens an occluded blood vessel has become prevalent for treating myocardial infarction. As a result, in recent years, the mortality rate due to myocardial infarction has a trend that slightly decreases in the long run. However, even if blood flow resumes for example, myocardial necrosis remains. Therefore, cardiac failure occurs in the future, and thus the death rate is very high. For example, there are studies showing that the 5-year survival rate of patients with chronic cardiac failure is only approximately 40%.

A technique of inserting an electrode in a blood vessel is known as one treatment for acute cardiac failure (for example, see Patent Document 1). Patent Document 1 describes that an electrical pulse stimulation is applied to parasympathetic nerves and/or sympathetic cardiac nerves using an electrode array positioned in a vein, in neuromodulation systems for treating acute heart failure syndromes.

CITATION LIST

Patent Documents

Patent Document 1: US 2014/0,142,590 A

SUMMARY

Technical Problem

However, although the technique described in Patent Document 1 is mentioned for treating cardiac failure, treatment for myocardial infarction is not considered at all. As described above, the morbidity rate for cardiac failure is very high when myocardial infarction occurs. Therefore, appropriate treatment at the time of myocardial infarction is thought to result in reduced mortality rate of cardiac failures.

In view of the foregoing, one object of several aspects of the present invention is to provide a control apparatus for treating myocardial infarction that can suitably perform treatment of myocardial infarction, and a control method for treating myocardial infarction.

Solution to Problem

A control apparatus for treating myocardial infarction according to one embodiment of the present invention, contains: a stimulation control unit that outputs a stimulation signal for reducing a myocardial workload to an electrode for stimulation inserted in a blood vessel running in the vicinity of the vagus nerve of a patient in order to stimulate the vagus nerve; a detecting unit that detects first biological information and second biological information of the patient; a setting unit that sets threshold information for determining a normal range of the first biological information and second biological information; and a determining unit that determines whether or not values of the detected first biological information and second biological information are within the normal range determined in the threshold information; wherein the stimulation control unit adjusts the intensity of the stimulation signal such that the values of the first biological information and second biological information are within the normal range, and the value of the second biological information is reduced by a predetermined ratio or more as compared to a value before the stimulation.

A control method for treating myocardial infarction according to one embodiment of the present invention allows the control apparatus for treating myocardial infarction, to perform the following: outputting a stimulation signal for reducing a myocardial workload to an electrode for stimulation inserted in a blood vessel running in the vicinity of the vagus nerve of a patient in order to stimulate the vagus nerve; detecting first biological information and second biological information of the patient; setting threshold information for determining a normal range of the first biological information and second biological information; determining whether or not values of the detected first biological information and second biological information are within the normal range determined in the threshold information; and adjusting the intensity of the stimulation signal such that the values of the first biological information and second biological information are within the normal range, and the value of the second biological information is reduced by a predetermined ratio or more as compared to a value before the stimulation.

Note that in the present invention, "unit", "means", "apparatus", or "system" do not simply refer to physical means, but also include cases where a function provided by the "unit", "means", "apparatus", or "system" is implemented by software. Furthermore, one function provided by the "unit", "means", "apparatus", or "system" may be implemented by two or more physical means or devices, or two functions of the "unit", "means", "apparatus", or "system" may be implemented by one physical means or device.

DESCRIPTION OF EMBODIMENTS

An embodiment of the present invention will be described below while referring to the drawings. However, the embodiment described below is merely an example and is not intended to exclude the application of various modifications and techniques not explicitly described below. In other words, the present invention can be implemented with various modifications without departing from a spirit thereof. Furthermore, in the following description of the drawings, the same or similar portions are denoted by the same or similar reference numerals. The drawings are schematic and do not necessarily correspond to actual dimensions, ratios, and the like. Portions with different dimensional relationships and ratios from each other may be included between drawings.

1. Overview

Myocardial infarction is a condition where blood does not sufficiently flow to the myocardium due to a thrombus formed in a blood vessel. When blood does not sufficiently flow to the myocardium, supply of oxygen to the myocardium does not meet the demand for oxygen in the myocardium, and thus a state of ischemia occurs. Therefore, reperfusion therapy that reopens an occluded blood vessel is generally used for treating myocardial infarction.

However, after the onset of myocardial infarction, myocardial ischemia continues until the blood vessel is reopened by reperfusion therapy. Therefore, a certain ratio of myocardium becomes necrotic during that time. Due to this necrosis, even if recovery is made from the onset of myocardial infarction, for example, many patients die from the onset of cardiac failure due to myocardial necrosis during myocardial infarction after a certain period of time.

Therefore, if myocardial necrosis can be suppressed at the onset of myocardial infarction, it is thought that subsequent onset of cardiac failure can be suppressed.

Herein, myocardial ischemia is caused due to the supply of oxygen to the myocardium not meeting the demand for oxygen of the myocardium. The aforementioned reperfusion therapy increases the supply of oxygen to the myocardium. However, myocardial necrosis can be suppressed if a treatment of suppressing the demand for oxygen in the myocardium is also performed in conjunction therewith.

In the control apparatus for treating myocardial infarction according to the present embodiment, an electrical stimulation is applied to the vagus nerve to reduce the heart rate, i.e., to reduce the myocardial workload. Therefore, the demand for oxygen in the myocardium is suppressed, so the occurrence of an ischemic condition is suppressed by using this method in combination with the aforementioned reperfusion therapy. As a result, the necrosis rate of the myocardium can be reduced.

On the other hand, any unreasonable application of stimulation to the vagus nerve may lead to a serious condition where the patient cannot recover due to a side effect such as coughing, a vomiting reflex, deterioration of hemodynamics due to bradycardia, or the like. Although it is conceivable that a doctor manually adjusts the amount of stimulation, the burden of continuing the adjustment for a long period of time is high. When any unreasonable amount of time is taken to adjust the amount of stimulation appropriate for the vagus nerve, the doctor cannot sufficiently deal with reperfusion therapy, which may lead to increased myocardial necrosis as a result.

Furthermore, if a suitable combination of electrodes for stimulating the vagus nerve must be selected from a large number of electrodes for stimulating the vagus nerve when applying an electrical stimulation, time is required for selecting the suitable electrodes when the doctor performs selection by hand. Therefore, myocardial necrosis may also increase during this time.

Therefore, the control apparatus for treating myocardial infarction according to the present embodiment can suitably stimulate the vagus nerve based on the condition of a patient without manually selecting electrodes for stimulating the vagus nerve or adjusting the amount of stimulation, so long as a doctor appropriately inserts a catheter for stimulating the vagus nerve.

Figure 1:
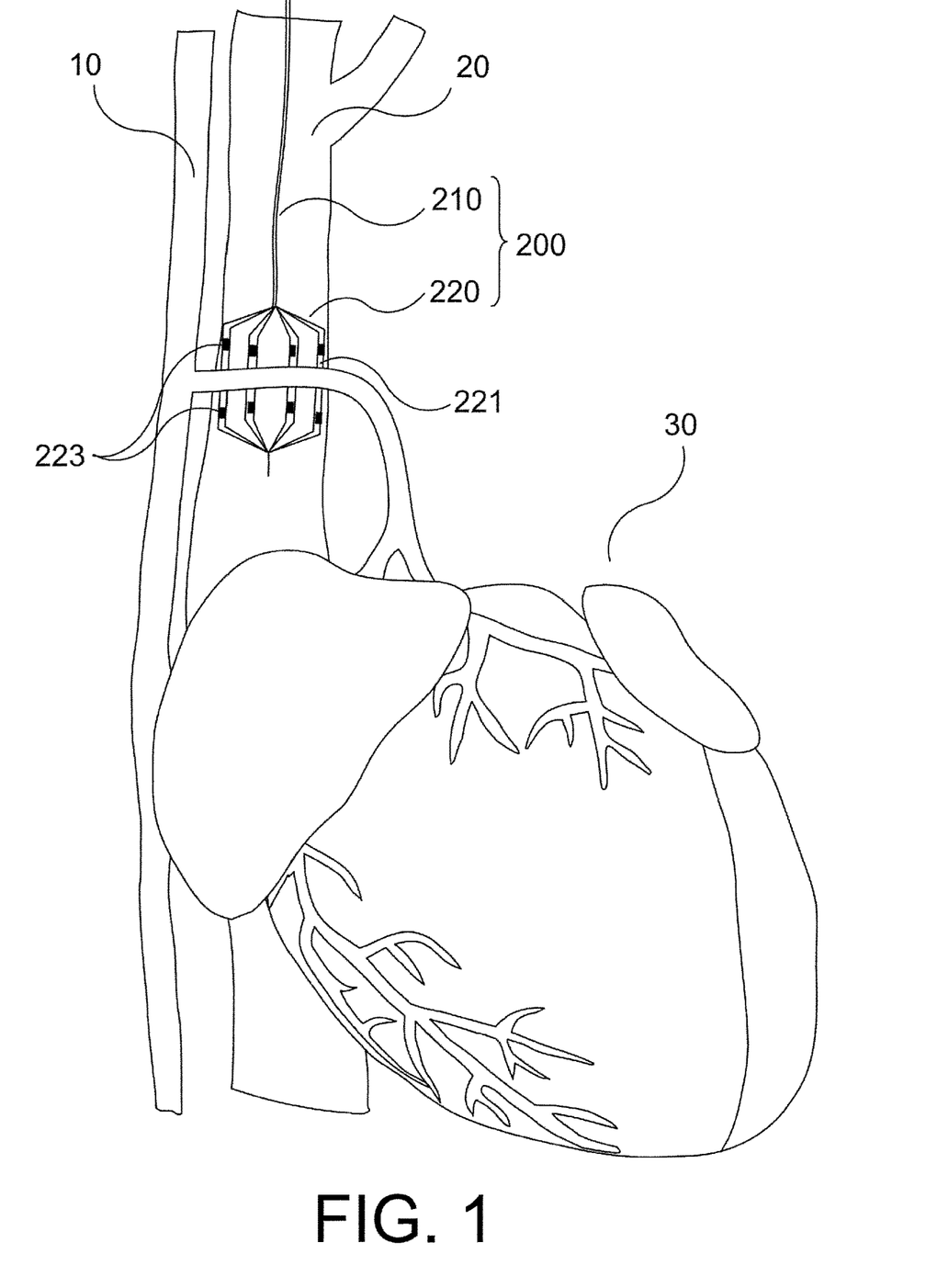
FIG. 1 is a diagram for describing a specific exemplary method of stimulating the vagus nerve according to an embodiment.

A specific exemplary method of applying an electrical stimulation to the vagus nerve will be described below while referring to FIG. 1. FIG. 1 is a diagram for describing a technique of applying an electrical stimulation to the vagus nerve 10 in order to treat myocardial infarction.

The vagus nerve 10 is a key parasympathetic nerve that passes from the brain to the chest through the neck. The vagus nerve 10 runs along the superior vena cava 20. Therefore, for example, when a catheter 200 for stimulating the vagus nerve is inserted in the superior vena cava 20 from a cervical vein, an electrical stimulation can be applied to the vagus nerve 10 via a vascular wall of the superior vena cava 20 from an electrode 223 for stimulation provided by the catheter 200 for stimulating the vagus nerve.

As described above, the vagus nerve 10 is a parasympathetic nerve, and therefore, stimulation of a parasympathetic nerve achieved by electrical stimulation causes a reduction in heart rate, a reduction in blood pressure, and the like. Therefore, if the vagus nerve 10 is stimulated within a suitable range, activity of the heart 30 is reduced, and therefore, the amount of oxygen consumed in the myocardium constituting the heart 30 can be reduced. As a result, the increase of myocardial necrosis is suppressed even under a condition where a blood vessel is occluded.

A configuration of the catheter 200 for stimulating the vagus nerve inserted in the superior vena cava 20 to stimulate the vagus nerve 10 will be simply described below. The catheter 200 for stimulating the vagus nerve is roughly divided into a tube unit 210 and a basket unit 220.

The tube unit 210 is a tubular unit that connects the basket unit 220 and the control apparatus for treating myocardial infarction. Transmission or the like of an electrical signal to the electrode 223 for stimulation provided by the basket unit 220 is performed via the tube unit 210.

The basket unit 220 is a part provided on a tip end of the catheter 200 for stimulating the vagus nerve, and contains a plurality of frame units 221 and a plurality of the electrodes 223 for stimulation attached to each frame unit 221.

Each of the plurality of frame units 221 serving as a framework for the basket unit 220 are connected at a connection portion with the tube unit 210 and a tip end portion on an opposite side thereof, so as to be able to open and close. In other words, the thickness of the basket unit 220 in a cross-sectional direction changes based on opening or closing of the frame unit 221. The basket unit 220 is set in a closed condition, in other words, a thin condition during an operation of inserting the catheter 200 for stimulating the vagus nerve into the superior vena cava 20 such that a doctor can easily insert the catheter 200 for stimulating the vagus nerve to a suitable position. On the other hand, when the basket unit 220 of the catheter 200 for stimulating the vagus nerve is inserted into a suitable position, for example, a position near a third rib in the superior vena cava, the doctor secures the position of the basket unit 220 by opening the frame unit 221 and bringing it into close contact with a blood vessel. Furthermore, the distance between the vagus nerve 10 and the electrode 223 for stimulation closest to the vagus nerve 10 is reduced thereby, and the distance is made constant. After treatment is completed, the basket unit 220 is closed again, so that the doctor can easily remove the catheter 200 for stimulating the vagus nerve.

A plurality of electrodes 223 for stimulation are respectively disposed on the plurality of frame units 221. The control apparatus for treating myocardial infarction, for example, applies an electrical stimulation on the vagus nerve 10 from a combination of the electrodes 223 for stimulation, and observes a resulting biological reaction. For example, processes are sequentially performed by applying an electrical stimulation from two electrodes 223 for stimulation disposed in a first frame unit 221, applying an electrical stimulation from two electrodes 223 for stimulation disposed in a second frame unit 221, and then applying an electrical stimulation from two electrodes 223 for stimulation disposed in a third frame unit 221. A biological reaction (such as heart rate) obtained as a result of applying the stimulations is recorded. Of these, the frame unit 221 where a combination of the electrodes 223 for stimulation having the largest reaction to the stimulation (for example, the largest reduction in heart rate) is considered to be the closest to the vagus nerve 10. Therefore, the control apparatus for treating myocardial infarction uses the electrode 223 for stimulation disposed in the frame unit 221 for stimulating the vagus nerve 10.

Note that in the example of the aforementioned description, a case was described of selecting two electrodes 223 for stimulation disposed on one frame unit 221 as an optimal combination of combinations of two electrodes 223 for stimulation disposed on frame units 221. However, the method of selecting the electrodes 223 for stimulation is not limited thereto. For example, it is also conceivable to use a combination containing one electrode 223 for stimulation provided by one frame unit 221 and one electrode 223 for stimulation provided by an adjacent frame unit 221 when stimulating the vagus nerve 10. In this case, a stimulation is sequentially applied to the vagus nerve 10 using every conceivable combination of the electrodes 223 for stimulation, and then of the combinations, a combination with the largest reaction with regard to the stimulation is preferably selected.

2. Functional Configuration

Figure 2:
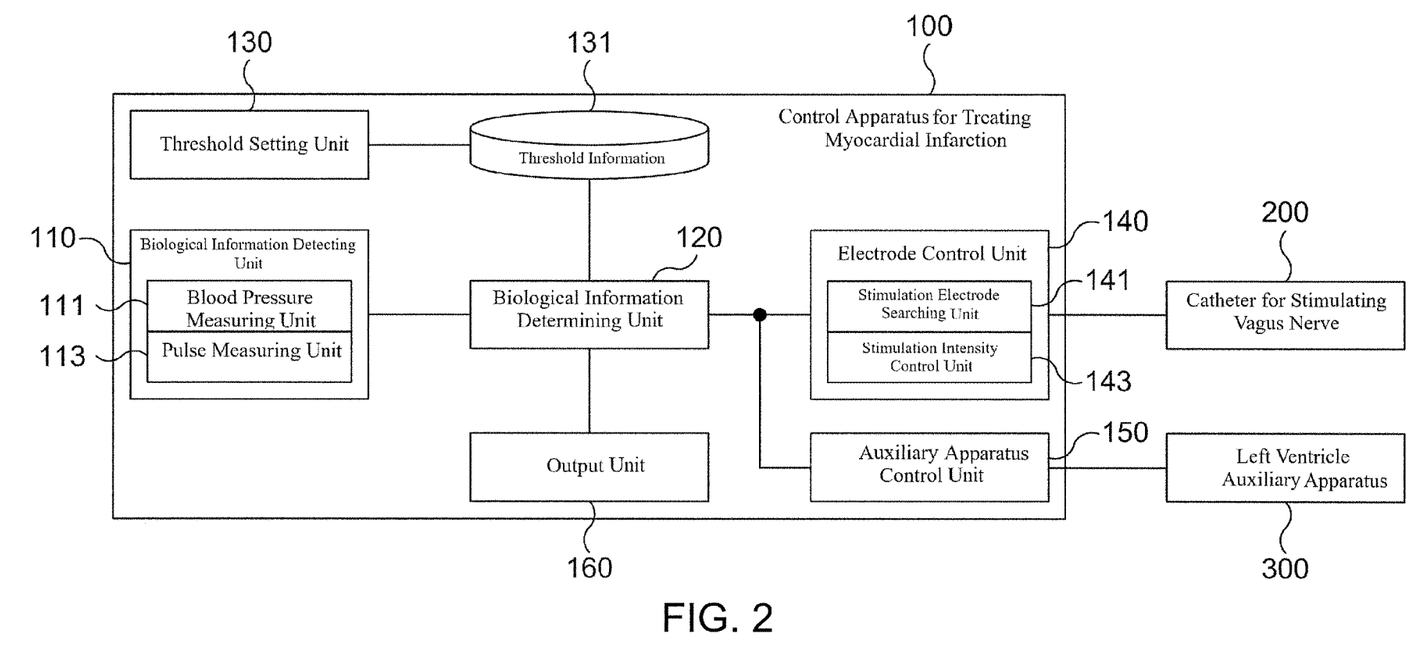
FIG. 2 is a diagram illustrating a functional configuration of a control apparatus for treating myocardial infarction according to an embodiment.

A functional configuration of a control apparatus 100 for treating myocardial infarction will be described below while referring to FIG. 2. As illustrated in FIG. 2, a control apparatus 100 for treating myocardial infarction can contain a biological information detecting unit 110, a biological information determining unit 120, a threshold setting unit 130, threshold information 131, electrode control unit 140, auxiliary apparatus control unit 150, and output unit 160.

The biological information detecting unit 110 detects various biological information such as heart rate, size of the heart, blood pressure, respiration, and the like from a human body. In FIG. 2, the biological information detecting unit 110 contains a blood pressure measuring unit 111 that measures blood pressure and a heart rate measuring unit 113 that detects a pulse.

In a search process for determining combinations of the electrodes 223 for stimulation used to stimulate the vagus nerve 10, a stimulation electrode searching unit 141 described later sequentially stimulates the vagus nerve 10 using the combinations of electrodes 223 for stimulation. At this time, the biological information determining unit 120 determines the magnitude of the biological reaction (for example, range of reduction in heart rate) caused by the stimulation. As a result, the stimulation electrode searching unit 141 can select a combination of the electrodes 223 for stimulation with the largest change in biological information to be used for stimulating the vagus nerve 10.

Furthermore, after the combination of electrodes 223 for stimulation used to stimulate the vagus nerve 10 for reducing the myocardial workload is determined, the biological information determining unit 120 determines whether or not a value of the biological information detected by the biological information detecting unit 110 falls within an appropriate range set by the threshold information 131. For example, the biological information determining unit 120 may determine whether or not heart rate, pulse amplitude, blood pressure, respiration, or the like, which are biological information, is at a lower limit value or higher set by the threshold information 131. The biological information determining unit 120 outputs the determination results to a stimulation intensity control unit 143 of the electrode control unit 140.

When the vagus nerve 10 is stimulated by the catheter 200 for stimulating the vagus nerve, the threshold setting unit 130 sets a range of values of biological information to be maintained (such as lower limit of blood pressure or pulse or the like) as threshold information 131. As a method of setting the threshold information 131, it is conceivable that a doctor may input a threshold value from an inputting interface such as a keyboard, touch panel, or the like based on daily blood pressure, chronic diseases, or the like of a patient, and then the threshold setting unit 130 stores the threshold information 131 in an arbitrary recording media based on the input.

The electrode control unit 140 performs various controls with regard to the catheter 200 for stimulating the vagus nerve having a plurality of the electrodes 223 for stimulation. For example, the electrode control unit 140 performs search of the combinations of the electrodes 223 for stimulation used to stimulate the vagus nerve 10 and adjusts the intensity of a stimulation signal used to stimulate the vagus nerve 10. Therefore, the electrode control unit 140 has the stimulation electrode searching unit 141 and a stimulation intensity control unit 143.

The stimulation electrode searching unit 141 performs a search process of determining which combination of the electrodes 223 for stimulation is used to stimulate the vagus nerve 10, of the plurality of electrodes 223 for stimulation provided by the catheter 200 for stimulating the vagus nerve. More specifically, the stimulation electrode searching unit 141 sequentially applies a stimulation signal with a predetermined intensity to the combination of electrodes 223 for stimulation selected from the plurality of electrodes 223 for stimulation. As a result, a stimulation is applied to the vagus nerve 10, and the biological information determining unit 120 determines a change in biological information caused in response to a reflex with regard to the stimulation. As a result, the stimulation electrode searching unit 141 determines the electrodes 223 for stimulation with the largest change in value of biological information to be used to stimulate the vagus nerve 10.

The stimulation intensity control unit 143 adjusts the intensity of a stimulation signal for stimulating the vagus nerve 10. More specifically, the stimulation intensity control unit 143 first stimulates the vagus nerve 10 by applying a stimulation signal with a predetermined intensity to the combination of the electrodes 223 for stimulation of the catheter 200 for stimulating the vagus nerve. The biological information determining unit 120 determines a change in biological information obtained in response to a reflex with regard to the stimulation. For example, when a reduction in heart rate is determined as a reflex of stimulating the vagus nerve 10, the stimulation intensity control unit 143 only has to increase the intensity of the stimulation signal if the rate of reduction in heart rate obtained by stimulation is smaller than a predetermined rate (such as several % to several ten %) and the obtained heart rate is higher than a lower limit value of a heart rate provided by the threshold information

131. On the other hand, if the obtained heart rate is lower than a lower limit value of a heart rate provided by the threshold information 131, the stimulation intensity control unit 143 only has to reduce the intensity of the stimulation signal. Based on this control, the control apparatus 100 for treating myocardial infarction reduces activity of the heart 30 within a range that does not affect life support (for example, range where heart rate does not fall below the lower limit value). Furthermore, at this time, the stimulation intensity control unit 143 may also determine blood pressure, and only has to stop output of the stimulation signal if a value of the blood pressure is lower than a lower limit value provided in the threshold information 131, for example.

The auxiliary apparatus control unit 150 performs control of a left ventricular assist apparatus 300. Herein, the left ventricular assist apparatus 300 is a pump that is inserted inside a left ventricle of the heart 30 as a catheter from a femur portion or the like of the patient for assisting circulation of blood. When the left ventricular assist apparatus 300 assists with circulation of blood, a myocardial workload is reduced while a reduction in blood pressure or the like caused by bradycardia due to vagus nerve stimulation or pumping failure of the heart 30 is suppressed. Therefore, the amount of oxygen consumption in the myocardium is reduced. As a result, myocardial necrosis is further suppressed from expanding. The auxiliary apparatus control unit 150 may control an operation of the left ventricular assist apparatus 300, such as the magnitude of assisting with transmission of blood by a pump or the like, based on the determination results of the biological information determining unit 120 as to whether or not a value of the biological information is properly maintained.

The output unit 160 notifies the doctor or patient of the biological information and the corresponding determination results. Displaying to a display device, audio output, or the like are conceivable as a notifying method for example.

3. Process Flow

Figure 3:
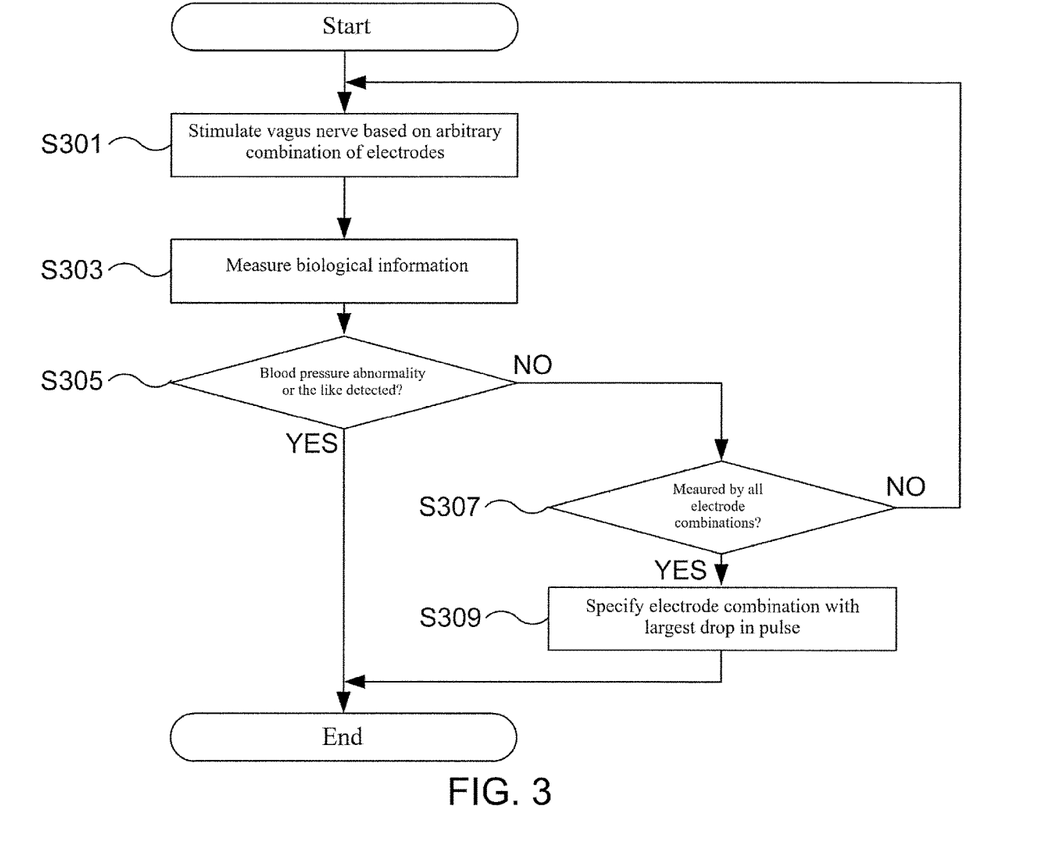
FIG. 3 is a flowchart showing the flow of a process where the control apparatus for treating myocardial infarction illustrated in FIG. 2 determines a combination of electrodes for stimulation used in stimulating the vagus nerve.
Figure 4:
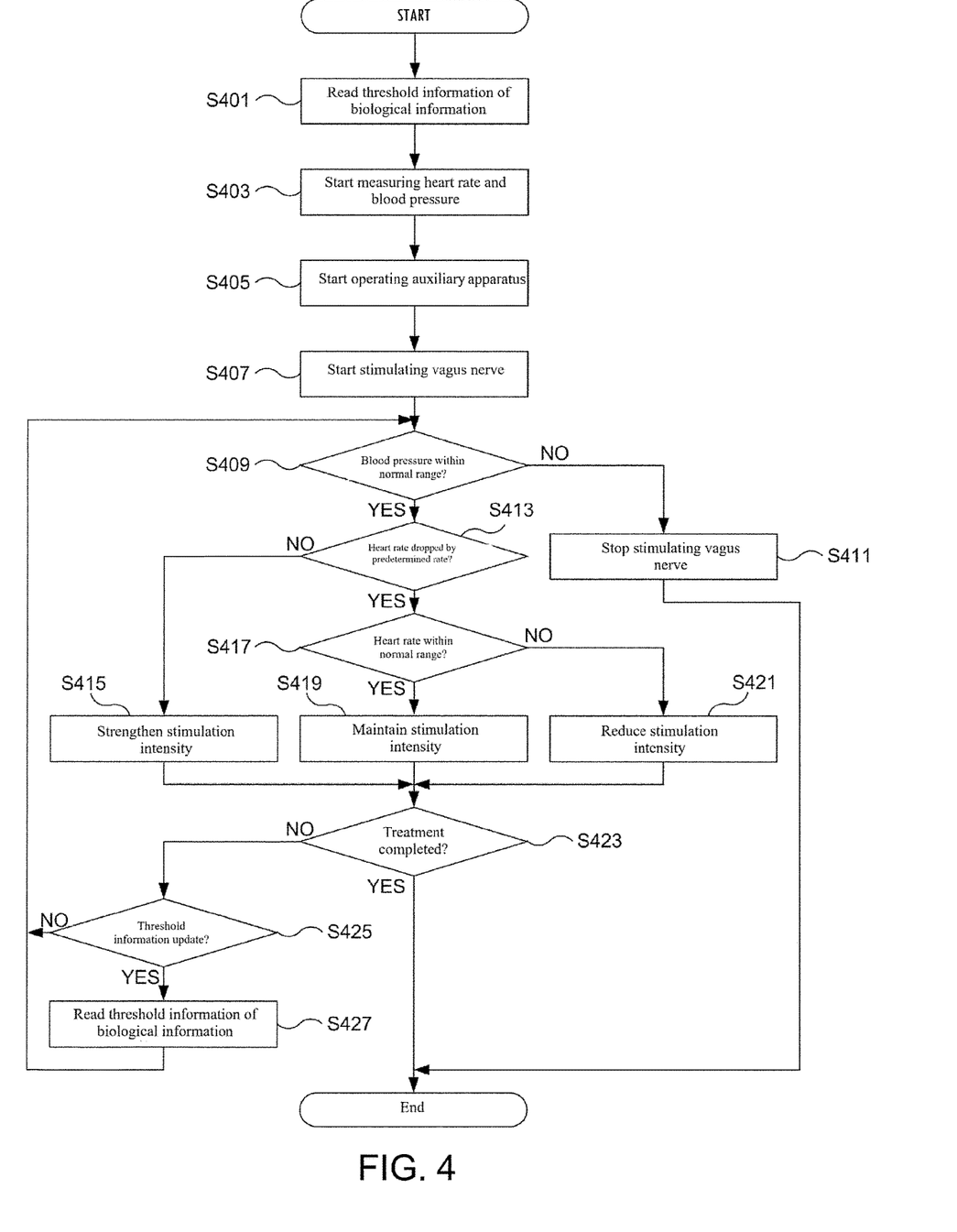
FIG. 4 is a flowchart showing the flow of a process for the control apparatus for treating myocardial infarction illustrated in FIG. 2 to perform treatment of myocardial infarction.

A process flow of the control apparatus 100 for treating myocardial infarction will be described below while referring to FIG. 3 and FIG. 4. FIG. 3 and FIG. 4 are flowcharts showing a process flow of the control apparatus 100 for treating myocardial infarction.

Note that process steps described later can be arbitrarily changed in order or performed in parallel within a scope where inconsistency does not occur in the process, and another step may be added between the process steps. Furthermore, a step described as one step for convenience can be divided into a plurality of steps to be performed, and a step described as being divided into a plurality of steps for convenience can be performed as one step.

3.1 Determination Process of Electrode 223 for Stimulation Used for

Stimulating Vagus Nerve 10

First, the following describes a determination process flow of the electrode 223 for stimulation used for stimulating the vagus nerve 10 by the control apparatus 100 for treating myocardial infarction after a doctor inserts the catheter 200 for stimulating the vagus nerve into the superior vena cava 20 and then expands the basket unit 220 while referring to FIG. 3. FIG. 3 is a flowchart showing a determination process flow of the electrode 223 for stimulation used for stimulating the vagus nerve 10.

When the catheter 200 for stimulating the vagus nerve is inserted into the superior vena cava 20, and the basket unit 220 of the catheter 200 for stimulating the vagus nerve is expanded such that the frame units 221 are pressed against an inner wall of a blood vessel, the stimulation electrode searching unit 14 stimulates the vagus nerve 10 by transmitting a stimulation signal to a combination of arbitrary electrodes 223 for stimulation, of a plurality of electrodes 223 for stimulation (S301). The biological information detecting unit 110 measures and records a change in biological information obtained after stimulating the vagus nerve 10, such as a change in pulse obtained from blood pressure, an electrocardiogram, pulse wave, or the like (S303). At this time, the biological information determining unit 120 determines whether or not a value of the blood pressure or the like, which is biological information, has dropped beyond a preset range (S305). If the blood pressure or the like has dropped beyond the preset value (Yes in S305), the control apparatus 100 for treating myocardial infarction ends the process. Note that end conditions of the process is not limited to a drop in blood pressure. For example, if body movement is detected or there is a complaint about pain from a patient, the control apparatus 100 for treating myocardial infarction can similarly end the process even if abnormal respiration is detected.

The stimulation electrode searching unit 141 applies a stimulation signal to the combinations of the electrodes 223 for stimulation in order (S301) and then measures biological information (S303) until changes in biological information with regard to all combinations of the electrodes 223 for stimulation are obtained (No in S307).

The biological information determining unit 120 determines the largest change in biological information (such as reduction in heart rate) from the obtained changes in biological information, and then determines the combination of the electrodes 223 for stimulation corresponding to the largest change in biological information as an appropriate combination used for stimulating the vagus nerve 10 (S309).

3.2 Adjustment Method of Stimulation Intensity of Vagus Nerve 10

Next, an adjustment method of a stimulation intensity when stimulating the vagus nerve 10 using the catheter 200 for stimulating the vagus nerve will be described while referring to FIG. 4. Note that in the example in FIG. 4, heart rate and blood pressure are used as biological information to be observed. However, arbitrary biological information such as respiration or the like can be used so long as the presence or absence of an obstacle to life support can be determined in the information.

First, the biological information determining unit 120 reads the threshold information 131 preset by the threshold setting unit 130 (S401). For example, lower limit values of the heart rate and blood pressure to be maintained can be included in the threshold information 131. Furthermore, the biological information detecting unit 110 starts measurement of biological information containing the heart rate and blood pressure (S403). Furthermore, the auxiliary apparatus control unit 150 starts an operation of the left ventricular assist apparatus 300 (S405). The electrode control unit 140 starts stimulating the vagus nerve 10 using the combination of the electrodes 223 for stimulation determined in the aforementioned process in 3.1 (S407).

The biological information determining unit 120 determines whether or not a value of the blood pressure, which is biological information detected by the biological information detecting unit 110, falls within a range set by the threshold information 131 (S409). If the value of the blood pressure is below the lower limit value set by the threshold information 131 (No in S409), the electrode control unit 140 stops output of the stimulation for stimulating the vagus nerve 10 (S411).

On the other hand, if the measured blood pressure is within the range set by the threshold information 131 (Yes in S409), the biological information determining unit 120 determines a value of the heart rate, which is biological information detected by the biological information detecting unit 110. More specifically, first, the biological information determining unit 120 determines whether or not the value of the heart rate is reduced by a predetermined ratio (for example, several % to several ten %) or more as compared to a value before applying stimulation (S413). As a result, if the heart rate is determined to not have sufficiently dropped (No in S413), the stimulation intensity control unit 143 increases the intensity of the stimulation to be applied to the vagus nerve 10, i.e., the intensity of the stimulation signal (S415). At this time, it is conceivable that the auxiliary apparatus control unit 150 also increases the output of a pump by the left ventricular assist apparatus 300.

As a result of the determination in S413, if the value of the heart rate is determined to be reduced by the predetermined ratio or more (Yes in S413), the biological information determining unit 120 determines whether or not the measured value of the heart rate is within the range set by the threshold information 131 (for example, whether or not the value is a lower limit value or higher) (S417). If the heart rate is within a normal range, the stimulation intensity control unit 143 and the left ventricular assist apparatus 300 do not change the intensity of the stimulation signal and output of the pump (S419).

On the other hand, if the measured heart rate is outside of the range set by the threshold information 131 (No in S417), it is determined that there may be an obstacle to life support. Therefore, the stimulation intensity control unit 143 adjusts the stimulation intensity, by reducing the intensity of the stimulation signal, for example (S421). The processes of S409 to S421 are repeated until treatment of myocardial infarction is completed (No in S423).

At this time, if the threshold setting unit 130 corrects the threshold information 131 based on an operation from the doctor or the like (Yes in S425), the biological information determining unit 120 only has to perform the processes from S409 to S421 once the corrected threshold information 131 is read (S427).

4. Hardware Configuration

Figure 5:
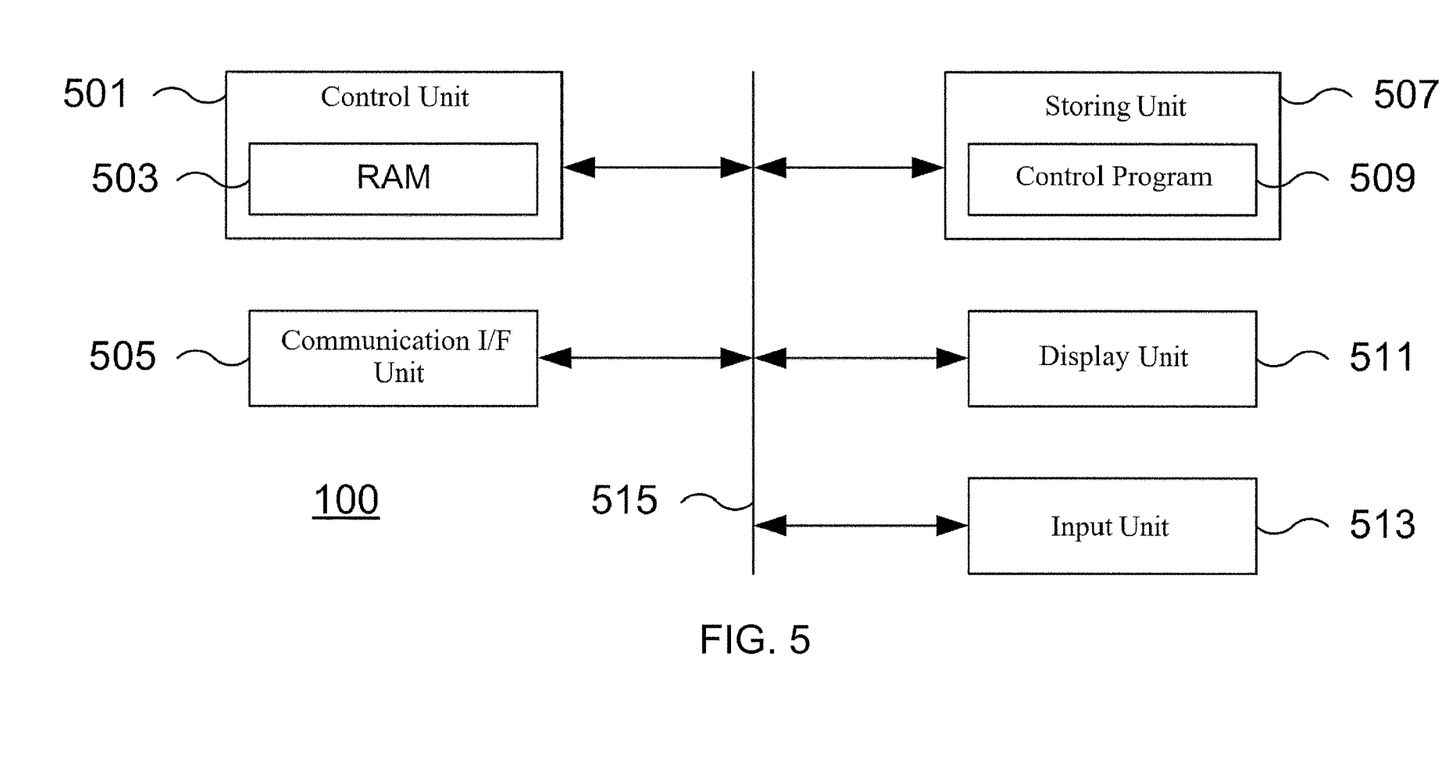
FIG. 5 is a diagram illustrating a specific example of the control apparatus for treating myocardial infarction illustrated in FIG. 2.

A hardware configuration where the control apparatus 100 for treating myocardial infarction can be implemented will be described below while referring to FIG. 5. The control apparatus 100 for treating myocardial infarction contains a control unit 501, a communication I/F unit 505, a storing unit 507, a display unit 511, and an input unit 513, and those units are connected via a bus line 515.

The control unit 501 contains a CPU (Central Processing Unit. Not shown here), a ROM (Read Only Memory. Not shown here), a RAM (Random Access Memory) 503, and the like. The control unit 501 is configured to execute a control program 509 stored in the storing unit 507 such that the processes related to each configuration illustrated in FIG. 2 can be performed. For example, the biological information detecting unit 110, biological information determining unit 120, threshold setting unit 130, electrode control unit 140, auxiliary apparatus control unit 150, and output unit 160 can be implemented as the control program 509 temporarily stored in the RAM 503 and then operated on the CPU.

Furthermore, the RAM 503 temporarily stores a portion or all of the input or output biological information, threshold information 131, or the like in addition to a code included in the control program 509. Furthermore, the RAM 503 is also used as a work area when the CPU executes various processes.

The communication I/F unit 505 is a device that communicates with an external device such as the catheter 200 for stimulating the vagus nerve or left ventricular assist apparatus 300. For example, it is conceivable that output of a stimulation signal to the catheter 200 for stimulating the vagus nerve, output of a control signal to the left ventricular assist apparatus 300, and the like are performed via the communication I/F unit 505.

The storing unit 507 is a non-volatile storing medium such as an HDD (Hard Disk Drive), a flash memory, and the like for example. The storing unit 507 stores an operating system (OS) for implementing functions as a general computer, the control program 509, and data required for executing these, such as biological information and the threshold information 131.

The display unit 511 is a display device for displaying various information to the doctor or the like who is handling the control apparatus 100 for treating myocardial infarction. Specific examples of the display unit 511 include liquid crystal displays, organic EL (Electro-Luminescence) displays, and the like. For example, it is conceivable that biological information measured by the biological information detecting unit 110, and determination results of the biological information determining unit 120 with regard to the biological information, and the like are displayed by the display unit 511.

The input unit 513 is a device for receiving various input operations from the doctor or the like who is operating the control apparatus 100 for treating myocardial infarction. Specific examples of the input unit 513 can include keyboards, mouses, touch panels, and the like. For example, the threshold information 131 is input from the input unit 513, and the threshold setting unit 130 can set the information based on the input.

5. Effect of Present Embodiment

As described above, the control apparatus 100 for treating myocardial infarction according to the present embodiment stimulates the vagus nerve 10 using the catheter 200 for stimulating the vagus nerve, and prompts a reduction in a myocardial workload using the left ventricular assist apparatus 300 if necessary. As a result, the amount of oxygen consumed in the myocardium is reduced and a blood vessel is opened by reperfusion therapy at the same time, and thus myocardial necrosis during myocardial infarction can be significantly reduced. The onset of cardiac failure after recovering from myocardial infarction is also expected to be reduced as a result.

Furthermore, when the vagus nerve is stimulated, bradycardia occurs, and therefore, circulation of blood weakens. Therefore, the left ventricular assist apparatus 300 is used by the auxiliary apparatus control unit 150 to assist with circulation of blood, such that a myocardial workload is reduced while a reduction in blood pressure or the like caused by bradycardia due to vagus nerve stimulation or pumping failure of the heart 30 is also suppressed. Therefore, the amount of oxygen consumption in the myocardium is reduced. As a result, myocardial necrosis is further suppressed from expanding.

Furthermore, when the stimulation intensity on the vagus nerve 10 is too strong, a reduction in blood pressure and the like may occur, which may lead to an obstacle to life support. Therefore, in the control apparatus 100 for treating myocardial infarction, the biological information is monitored by the biological information detecting unit 110, and the stimulation intensity on the vagus nerve 10 and operation of the left ventricular assist apparatus 300 are automatically adjusted such that a value of the biological information falls within a range set by the threshold information 131. As a result, stimulation on the vagus nerve 10 can be suitably adjusted without relying on the ability of a doctor or the like, and without a doctor performing long-term treatment.

6. Appendix

The embodiments described above is used to facilitate understanding of the present invention but is not intended, to limit the present invention. Elements included in the embodiment, arrangements, material, conditions, shapes, sizes, and the like thereof are not limited to those examples and can be appropriately changed. Furthermore, configurations shown in different embodiments can be partially substituted by or combined with each other.

REFERENCE SIGNS LIST

100: Control apparatus for treating myocardial infarction
110: Biological information detecting unit
111: Blood pressure measuring unit
113: Pulse measuring unit
120: Biological information determining unit
130: Threshold setting unit
131: Threshold information
140: Electrode control unit
141: Stimulation electrode searching unit
143: Stimulation intensity control unit
150: Auxiliary apparatus control unit
160: Output unit
200: Catheter for stimulating vagus nerve
210: Tube unit
220: Basket unit
221: Frame unit
223: Electrode for stimulation
300: Left ventricular assist apparatus
501: Control unit
503: RAM
505: Communication interface (I/F) unit
507: Storing unit
509: Control program
511: Display unit
513: Input unit
515: Bus line

What is claimed is:

1. A control apparatus for treating myocardial infarction, comprising:
a stimulation control unit configured to output a stimulation signal to an electrode for stimulation provided on a first catheter inserted in a vena cava running along the vagus nerve of a patient in order to stimulate the vagus nerve;
a detecting unit configured to detect blood pressure and heart rate of the patient;
a memory configured to store threshold information that defines a normal range of the blood pressure and heart rate;
an auxiliary apparatus control unit coupled to a pump inserted inside a left ventricle of a heart of the patient as a second catheter through an artery of the patient and configured to control the pump to assist circulation of blood with reducing left ventricular workload; and
a determining unit configured to determine whether or not values of the detected blood pressure and heart rate are within the normal range determined in the threshold information; wherein
the stimulation control unit is configured to output the stimulation signal such that the value of the heart rate is reduced, when the values of the blood pressure and the heart rate are within the normal range, and
the stimulation control unit is configured to stop output of the stimulation signal, when the value of the blood pressure or the heart rate deviates from the normal range.

2. The control apparatus for treating myocardial infarction according to claim 1, further comprising:
an electrode searching unit configured to determine from a plurality of electrodes for stimulation a combination of the electrodes for stimulation; wherein
the electrode searching unit configured to sequentially output the stimulation signal to a combination of a portion of the plurality of electrodes for stimulation, and
of changes in the heart rate when output to each combination of the plurality of electrodes for stimulation, a combination of electrodes for stimulation with the largest change in the heart rate is set as a combination of electrodes for stimulation.

3. The control apparatus for treating myocardial infarction according to claim 1, wherein the auxiliary apparatus control unit is configured to control the pump such that the value of the blood pressure is within the normal range.

4. The control apparatus for treating myocardial infarction according to claim 1, wherein the stimulation control unit is configured to adjust the intensity of the stimulation signal such that the value of the blood pressure is within the normal range, and the value of the heart rate is reduced by a predetermined ratio or more as compared to a value before the stimulation.

5. The control apparatus for treating myocardial infarction according to claim 1, wherein the auxiliary apparatus control unit is configured to control the pump such that left ventricular workload is reduced and the value of the blood pressure is within the normal range in accordance with the values of the blood pressure.

6. A control method for treating myocardial infarction performed by the control apparatus for treating myocardial infarction, the method comprising:
outputting a stimulation signal to an electrode for stimulation provided on a first catheter inserted in a vena cava running along the vagus nerve of a patient in order to stimulate the vagus nerve;
detecting blood pressure and heart rate of the patient;
storing threshold information which defines a normal range of the blood pressure and heart rate;
controlling a pump that is inserted inside a left ventricle of a heart of the patient as a second catheter through an artery of the patient and coupled to the control apparatus to assist circulation of blood with reducing left ventricular workload;
determining whether or not values of the detected blood pressure and heart rate are within the normal range determined in the threshold information; and
outputting the stimulation signal such that the value of the heart rate is reduced, when the values of the blood pressure and the heart rate are within the normal range, and
stopping output of the stimulation signal, when the values of the blood pressure or the heart rate deviates from the normal range.

* * * * *